(12) United States Patent
Dmitrieva et al.

(10) Patent No.: US 10,353,461 B2
(45) Date of Patent: Jul. 16, 2019

(54) EVALUATING CLINICIAN

(71) Applicant: KONINKLIJKE PHILIPS N.V., Eindhoven (NL)

(72) Inventors: Julia Dmitrieva, Bothell, WA (US); Eric Cohen-Solal, Ossining, NY (US); Gabriel Ryan Mankovich, Boston, MA (US); Yuechen Qian, Lexington, MA (US)

(73) Assignee: Koninklijke Philips N.V., Eindhoven (NL)

( * ) Notice: Subject to any disclaimer, the term of this patent is extended or adjusted under 35 U.S.C. 154(b) by 213 days.

(21) Appl. No.: 15/316,288

(22) PCT Filed: Jun. 16, 2015

(86) PCT No.: PCT/IB2015/054538
§ 371 (c)(1),
(2) Date: Dec. 5, 2016

(87) PCT Pub. No.: WO2015/193806
PCT Pub. Date: Dec. 23, 2015

(65) Prior Publication Data
US 2017/0192502 A1    Jul. 6, 2017

Related U.S. Application Data

(60) Provisional application No. 62/013,050, filed on Jun. 17, 2014.

(51) Int. Cl.
*A61B 5/00* (2006.01)
*G06F 3/01* (2006.01)
(Continued)

(52) U.S. Cl.
CPC .............. *G06F 3/013* (2013.01); *A61B 3/113* (2013.01); *A61B 3/18* (2013.01); *A61B 5/161* (2013.01);
(Continued)

(58) Field of Classification Search
CPC ......... G06F 3/013; A61B 5/161; A61B 5/165; A61B 3/18; A61B 3/113
See application file for complete search history.

(56) References Cited

U.S. PATENT DOCUMENTS 6,111,580 A * 8/2000 Kazama .................. G06F 3/017
340/575
2007/0173699 A1   7/2007 Mathan et al.
(Continued)

FOREIGN PATENT DOCUMENTS

JP    2008219286 A    9/2008

OTHER PUBLICATIONS

Holmqvist, K. et al., "Eye Tracking: A comprehensive guide to methods and measures", Oxford University Press, 2011, ISBN: 9780199697083.

*Primary Examiner* — Max F Hindenburg

(57) ABSTRACT

A system includes (100) includes a display (112) that sequentially displays images from an image data set at a predetermined rate, an optical attention monitoring device (120) that senses a characteristic indicative of a clinician's attention to each displayed image of the image data set, and a processor (106) that executes an attention detection module (118) that detects a lapse in attention with respect to one or more of the displayed images based on the sensed characteristic indicative of the clinician's attention and generates a signal indicating the one or more of the displayed images.

17 Claims, 3 Drawing Sheets

Figure 1:
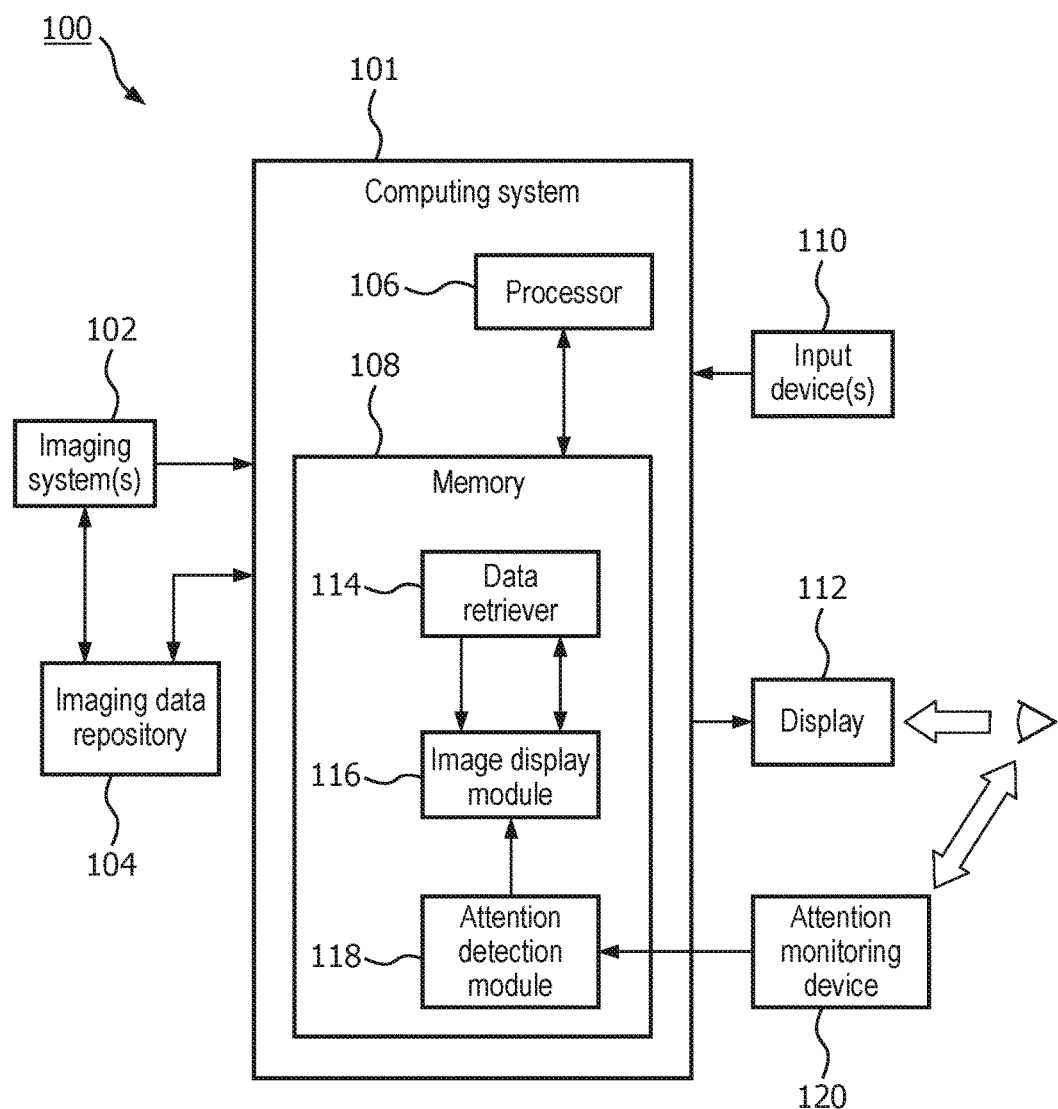

(51) Int. Cl.
  *A61B 3/113* (2006.01)
  *A61B 5/16* (2006.01)
  *G11B 27/00* (2006.01)
  *A61B 3/18* (2006.01)
  *G06F 3/03* (2006.01)
  G06F 3/0485 (2013.01)

(52) U.S. Cl.
  CPC .............. *A61B 5/165* (2013.01); *A61B 5/168* (2013.01); *G06F 3/012* (2013.01); *G06F 3/0304* (2013.01); *G11B 27/00* (2013.01); *G11B 27/007* (2013.01); *A61B 5/16* (2013.01); *G06F 3/011* (2013.01); *G06F 3/0485* (2013.01)

(56) References Cited

U.S. PATENT DOCUMENTS

| | | |
|---|---|---|
| 2007/0265507 A1 | 11/2007 | De Lemos |
| 2008/0048931 A1 | 2/2008 | Ben-Ari |
| 2009/0150821 A1 | 6/2009 | Mathan |
| 2011/0273731 A1 | 11/2011 | Haikin et al. |
| 2013/0340006 A1 | 12/2013 | Kwan |
| 2015/0043033 A1 | 2/2015 | Sugimoto |
| 2015/0192992 A1 | 7/2015 | Di Censo et al. |

* cited by examiner

EVALUATING CLINICIAN

CROSS-REFERENCE TO PRIOR APPLICATIONS

This application is the U.S. National Phase application under 35 U.S.C. § 371 of International Application No. PCT/IB2015/054538, filed on Jun. 16, 2015, which claims the benefit of U.S. Provisional Application No. 62/013,050, filed on Jun. 17, 2014. This application is hereby incorporated by reference herein.

The following generally relates to evaluating clinician attention during display of imaging data sets.

Medical imaging provides useful information about the interior characteristics (e.g., anatomical tissue, material flow, etc.) of a subject under examination. In some instances, clinicians view sequences of hundreds of images corresponding to multiple patients while analyzing patient data. Such images have been viewed in a continuous cinematic loop in which each image is sequentially visually displayed based on a predetermined rate for a predetermined amount of time. With such display, any image may provide crucial visual information regarding a particular disease and/or state of a patient.

If a clinician's attention is disrupted for even a short period of time (e.g., a blink), an important image in the sequence may be missed, which could result in misdiagnosis. Currently, a clinician must voluntarily repeat sequences that the clinician feels were not thoroughly evaluated. Unfortunately, this depends on the clinician's self-awareness of his/her particular state of mind, and the clinician's willingness to spend additional time reviewing the sequence. Thus, there is an unresolved need for an approach to facilitate a clinician with determining whether an image should be visually displayed for review again.

Aspects described herein address the above-referenced problems and others. In one aspect, a system includes a display that sequentially displays one or more images from an image data set at a predetermined rate, an optical attention monitoring device that senses a characteristic indicative of a clinician's attention to the one or more images of the image data set; and a processor that executes an attention detection module (118) that detects a lapse in attention with respect to the one or more of the images based on the sensed characteristic indicative of the clinician's attention and generates a signal indicating a relationship between the lapse in attention and the one or more images.

In another aspect, a method includes sequentially displaying images from an image data set at a predetermined rate, monitoring a characteristic indicative of a clinician's attention to a displayed image of the image data set; detecting a lapse in attention of the clinician to at least one of the displayed images based on the characteristic indicative of the clinician's attention; and re-displaying the at least one of the displayed images in response to the detecting of the lapse in attention.

In another aspect, a computer readable storage medium is encoded with computer readable instructions, which, when executed by a processor, causes the processor to: sequentially display images from a volumetric image data set at a predetermined rate, monitor a characteristic indicative of a clinician's attention to the displayed image of the volumetric image data set; detect a lapse in attention to at least one of the displayed images based on the characteristic indicative of the clinician's attention; and identify the at least one of the displayed images to re-display in response to detecting of the lapse in attention.

The invention may take form in various components and arrangements of components, and in various steps and arrangements of steps. The drawings are only for purposes of illustrating the preferred embodiments and are not to be construed as limiting the invention.

FIG. 1 schematically illustrates a computing system with an attention detection module in connection with an imaging system(s) and a data repository.

Figure 2:
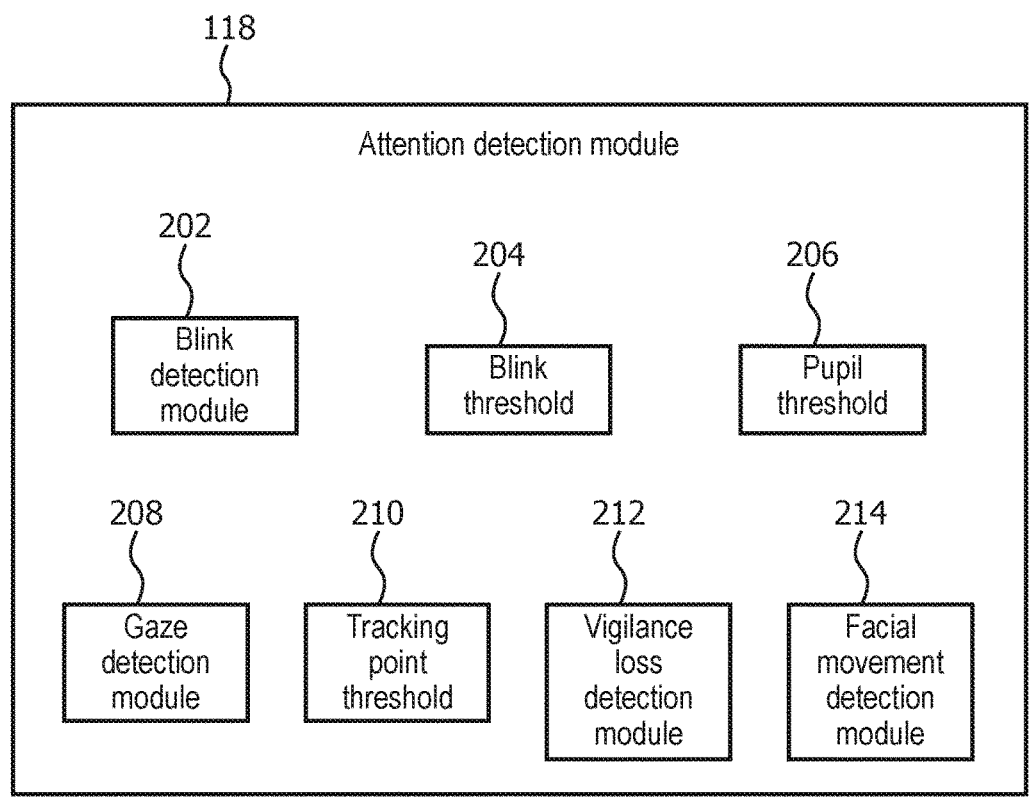

FIG. 2 schematically illustrates an example of the attention detection module.

Figure 3:
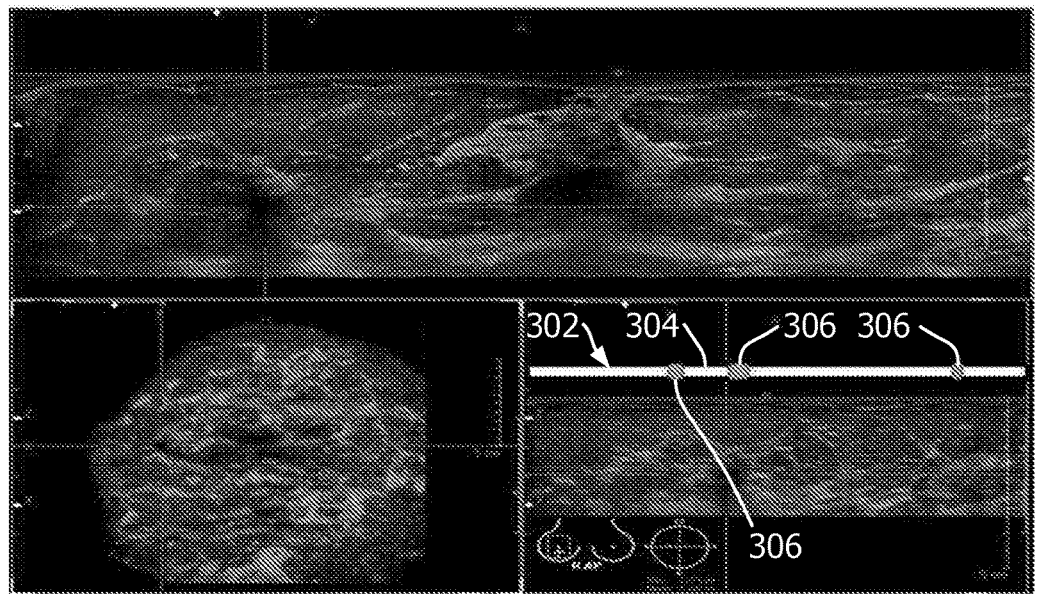

FIG. 3 schematically illustrates displayed data including an attention status bar.

Figure 4:
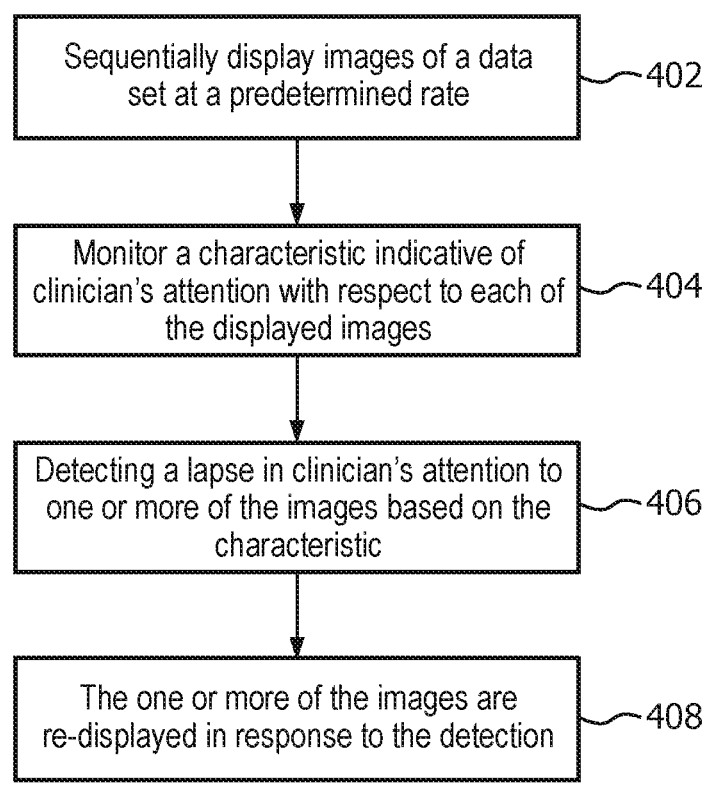

FIG. 4 illustrates a method for detecting a lapse of attention and replaying images presented during the lapse of attention.

FIG. 1 schematically illustrates a system 100 in connection with an imaging system(s) 102 and/or an image data repository 104. Imaging data may be stored by and/or transferred between the computing system 101, the imaging system(s) 102, and/or the image data repository 104 in standard formats such as Digital Imaging and Communications in Medicine (DICOM), Health Level 7 (HL7), and/or other standard formats, and/or non-standard, proprietary, and/or other format.

The imaging system(s) 102 can include one or more of an ultrasound (US), a computed tomography (CT), a magnetic resonance (MR), a positron emission tomography (PET), a single-photon emission computed tomography (SPECT), and/or other imaging system. The image data repository 104 can include one or more of a picture archiving and communication system (PACS), a radiology information system (RIS), a hospital information system (HIS), and/or other data repository.

The computing system 101 includes one or more processors 106 (e.g. microprocessor, central processing unit, controller, etc.) and computer readable storage medium ("memory") 108 (i.e., physical memory and other non-transitory storage medium, and excluding transitory medium). The computing system 101 interfaces with an input device(s) 110 such as a keyboard, a mouse, a microphone, a touchscreen, etc. and an output device such as a display 112, a filmer, a printer, etc.

The computer readable storage medium 108 is encoded with computer readable instructions, which, when executed by the one or more processors 106 cause the computing system 101 to carry out the various functions described herein. The one or more processors 106 can additionally or alternatively execute instructions carried by a carrier wave, a signal and other transitory storage medium. In the illustrated embodiment, the computer readable storage medium 108 includes several software modules, including a data retriever 114, an image display module 116 and an attention detection module 118.

The data retriever 114 receives a signal, as an input, via the input device(s) 110 and/or processor 106, identifying an imaging data set to retrieve. The computing system 101, in one example, first visually presents through the display 112 a list of stored patient studies, from which a clinician can select an imaging data set to load. The selected imaging data set may be an initial imaging data set of a patient to be read or a follow-up imaging data set of the patient for reading and comparison with a previously generated data set of the patient. The imaging data set comprises a plurality of images that can be displayed in a sequence.

The display 112 sequentially displays images from the imaging data set. The images are received from the image display module 116. A rate at which each image is displayed is predetermined and interpreted by the image display module 116. A rate of image display can vary based on conditions such as user input, etc. An example of a predetermined rate of display is one image per second. However, other rates are also contemplated herein. For example, an image can be presented at a faster or slower rate. The image display module 116 additionally determines a subset of already displayed images to display again (as described in more detail below) based on an observed attention characteristic of the clinician.

The optical attention monitoring device 120 monitors a clinician's visual attention to each displayed image. The optical attention monitoring device 120 provides information regarding eye-related activity such as gaze measurements, eye movements, events of saccades and fixations, pupil and iris tracking, and center/size estimation of pupils. In one example, the optical attention monitoring device 120 is a remote eye tracker placed in front of the display 112 facing a clinician, remotely tracking eye features. Alternatively, the optical attention monitoring device 120 can be a head-mounted/mobile eye tracker that records a scene as viewed by the clinician. In another example, the optical attention monitoring device 120 can be a camera that obtains data related to facial orientation and facial features.

An optical attention monitoring device 120 is a physical device such as an optical sensor that senses a characteristic indicative of the clinician's visual attention to each displayed image. The attention detection module 118 evaluates the signal from the optical attention monitoring device 120 and detects a lapse in attention for an image, if one exists, based on the signal. The signal, for example, includes information such as attention related to eye contact along a line of sight to the displayed images, direction of eye gaze at the displayed images, the capture of facial characteristics in relation to the displayed images, and/or other information.

The optical attention monitoring device can compensate for a clinician wearing glasses, contact lenses, and any other type of vision correction device in the detection of the lapse of attention. As shown in FIG. 1, the optical attention monitoring device 120 and the display 112 are separate from the computing system 101 and the imaging system 102. However, the optical attention monitoring device 120 and/or the display can be integrated within the computing system 101 or the imaging system 102.

Turning to FIG. 2, an example of the attention detection module 118 is illustrated.

In this example, the attention detection module 118 includes one or more of a blink detection module 202, a gaze detection module 208, a vigilance loss detection module 212 or a facial movement detection module 214. In a variation, the attention detection module 118 may include more or less modules, including a same module and/or a different module.

The blink detection module 202 detects blinks of an eye, measures a time period of blink duration, and compares the time period of blink duration to a threshold. As used herein, the time period of blink duration is a time period from an eyelid beginning to close with a first saccade, and ending with the eyelid fully opening after a second saccade. Based on eyelid movement data provided by the attention monitoring device, the event detection module determines the time period of blink duration irrespective of whether the clinician is wearing glasses, contacts and/or another vision correction device.

Once the time period of blink duration is known, the blink detection module 202 compares the time period to a predetermined blink threshold 204. If the blink duration exceeds the predetermined blink threshold 204 (e.g. the eye has been closed for a sufficient amount of time), the blink detection module 202 transmits a signal, which indicates the eye has been closed for a sufficient amount of time, to the image display module 116. The signal indicates the blink caused a lapse of attention and includes time data indicative of the lapse.

The blink detection module 202, alternatively or additionally, analyzes a visual representation of a pupil captured by the optical attention monitoring device 120. For example, the optical attention monitoring device 120 may track a clinician's eyeball while the attention detection module analyzes pupil data sent by the attention monitoring device. During a blink, the eyelid may cover a pupil, resulting in the optical attention monitoring device 120 losing pupil data due to a lack of eyeball exposure. A pupil threshold 206 can be retrieved (i.e. 30-80 milliseconds (ms), such as 45 ms, 50 ms, 52 ms, etc.) that causes the attention detection module 118 to ignore loss of pupil data for a length of time up to the pupil threshold 206, before sending a signal indicating a lapse in attention.

The gaze detection module 208 analyzes a gaze of a clinician with respect to the displayed images. If the gaze of the clinician is focused on the displayed images, the clinician is determined to be adequately focused with no lapse in attention. However, if the gaze is not focused on the displayed images, the clinician is not providing adequate attention. The attention detection module 118 transmits a signal to the image display module to adjust image display and/or repeat at least a segment of the displayed images.

In determining a clinician's attention, the gaze detection module 208 tracks a clinician's eye at a frequency from thirty (30) to hundreds of eye tracking points per second. A clinician's gaze location may drift even though the clinician has not blinked. The clinician's gaze location may not be fixated on the individual frame of the consecutive images, but instead fixated on a location outside of the image frame or in a non-pertinent part of the image frame. When an errant gaze location is detected, the attention detection module 118 may send a signal indicating an errant gaze to the image display module 116. The attention detection module 118 indicates a sub-set of images to re-display. The image display module 116 re-displays the sub-set.

The gaze detection module 208 additionally analyzes gazes detected by the optical attention monitoring device 120 to determine whether an unsatisfactory number of eye tracking points were directed to the displayed images. Some tracking points may directed toward the displayed images while others may be directed toward a background of the displayed images or the controls of the input device 110. The gaze detection module 208 compares the number of tracking points directed at the displayed images to a tracking point threshold 210.

If a number of tracked locations greater than the threshold are focused on the displayed images, the gaze detection module 208 does not determine that a lapse in attention has occurred and does not send a signal to the image display module to replay images. However, if a number of tracked locations less than the threshold are focused on the displayed images, the attention detection module 118 determines that a lapse in attention has occurred and sends a signal to the image display module to replay images.

The gaze detection module 208 can analyze image data before presentation to determine likely regions of abnormalities on the images. The clinician's viewing location can be tracked to make sure the clinician has viewed these likely regions. For example, image regions within the displayed images may be pre-identified using artificial intelligence techniques or algorithms based on expert radiologists' interpretation techniques. The gaze detection module 208 analyzes viewing locations obtained by the optical attention monitoring device 120. The gaze detection module 208 checks to see that the viewing locations match the pre-identified likely regions of abnormalities.

Alternatively, the gaze detection module 208 compares a clinician's viewing location with known abnormalities on the displayed images. For example, the displayed images can represent a follow-up case, and the clinician may be viewing previously-annotated images. The annotations provide specific locations of abnormalities within the displayed images that are known to the attention detection module 118. The gaze detection module 208 analyzes the gaze of the clinician in relationship to the displayed images and the annotations of the displayed images to determine if gaze points are directed toward the areas of the displayed images identified by the annotations.

Alternatively, computer-aided detection (CAD) techniques can be used to detect areas that are abnormal or suspicious. The gaze points can be compared to the image data to determine if a clinician has reviewed the areas predetermined to be abnormal.

A vigilance loss detection module 212 detects loss of vigilance of a clinician. A loss of vigilance occurs when a clinician has too high of a mental workload is inadequately rested or is distracted. In one instance the vigilance loss detection module 212 establishes a baseline measurement at a first period of time. The period of time can be in the beginning of a clinician's work day. The baseline measurement can be computed by obtaining a distribution of blink durations over the course of the baseline period measurement. During other times of the work day, a clinician's attention can be analyzed and compared to the baseline measurement. If a discrepancy exists beyond a predetermined threshold, a loss of vigilance can be determined and the attention detection module 118 can adjust display of the images.

Alternatively, the vigilance loss detection module 212 can detect a loss of vigilance using a measure of proficiency based on the clinician scanning images for suspicious regions. The vigilance loss detection module 212 measures the scanning path during the first period of time at the beginning of a clinician's work day. When a clinician is losing vigilance, the scan path may become erratic and/or drift from a usual gaze path. A significant departure from the originally established path during the first time period could indicate a loss of vigilance. The loss of vigilance could indicate a sub-optimal review of the study. The vigilance loss detection module 212 can indicate to a clinician that rest is required for a given period of time, and present the images to the image display module after the rest period of time has ended.

A facial movement detection module 214 determines if a face of the clinician is focused on the display. For example the facial movement detection module 214 may employ a facial recognition detection algorithm to determine if the face is focused along a line of sight to the image. If no facial features are detected as focused on the line of sight, the facial movement detection module 214 may send a signal to the image display module 116 to pause or stop the image displayed on the display 112.

The image display module 116 re-displays images via the display 112 based on signals received from the attention detection module 118.

Turning to FIG. 3, the image display module 116 presents, in one instance, a graphical attention status bar 302. The graphical attention status bar 302 comprises a first bar 304 and one or more segments 306 (three shown in the illustrated example). The first bar 304 represents the displayed images, and the one or more segments 306 indicate images where the clinician's attention had lapsed and that images were not viewed thoroughly.

In one instance, the image display module 116 allows a clinician to interact with the graphical attention status bar 302 via a cursor, stylus, finger or other selection device. During or after a complete sequence of image data has been displayed, the image display module 116 analyzes signals sent from the event detection module. The image display module 116 presents missed images based on clinician interactions with the graphical attention status bar 302. For example, a clinician can select a portion of the graphical attention status bar 302 that indicates missed images. The image display module 116 retrieves missed image data corresponding to a selected segment of the graphical attention status bar 302, and replays the selected images for the clinician.

In another instance, the image display module 116 may actively adjust playback as images are displayed. If any signal is received from the event detection module indicating that a clinician's attention is not focused on the display, the image display module 116 may replay the missed image data as soon as the clinician's attention is refocused. The replay may be accompanied by audio feedback indicating that missed frames are being replayed.

FIG. 4 schematically illustrates a method for detecting a lapse of attention and replaying images presented during the lapse of attention.

At 402, images from a data set are sequentially displayed at a predetermined rate.

At 404, a characteristic indicative of a clinician's attention to each displayed image of the volumetric image data set is monitored.

At 406, a lapse in attention for one or more of the images is detected based on the monitored characteristic.

At 408, the one or more of the images are re-displayed in response to the detection of the lapse in attention.

The above methods may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A system, comprising:
 a display for sequentially displaying one or more images from an image data set at a predetermined rate;
 an optical attention monitoring device for sensing a characteristic indicative of a clinician's attention to the one or more images of the image data set; and
 a processor for executing an attention detection module for detecting a lapse in attention with respect to the one or more of the images based on the sensed characteristic indicative of the clinician's attention and generating a signal indicating a relationship between the lapse in attention and the one or more images; and an image display module for re-displaying one or more images in response to the signal, characterized in that the attention detection module comprises a blink detection module for analyzing a time period of blink duration or an exposure of a pupil as the characteristic indicative of the clinician's attention and for determining the lapse based on the time period of blink duration exceeding a predetermined blink threshold or based on a time period of pupil loss exceeding a predetermined pupil threshold.

2. The system of claim 1, further comprising:

an image display module for superimposing a graphical attention status bar over the one or more images on the display, wherein the attention status bar includes a first bar indicating an order of the sequential display of the one or more images and one or more segments superimposed over the first bar that correspond to the one or more images displayed during the lapse in attention.

3. The system of claim 2, wherein the image display module is configured to re-display at least one of the one or more images in response to an input indicative of a selection of at least one of the one or more segments by the clinician.

4. The system of claim 1, further comprising:

an image display module re-displaying only the one or more of the images displayed during the lapse in attention in response to the signal.

5. The system of claim 1, further comprising:

an image display module for re-displaying the one or more images in response to the signal.

6. The system of claim 1, further comprising:

an image display module for re-displaying a clinician selected sub-set of one or more of the displayed images in response to the signal.

7. The system of claim 1, wherein the attention detection module comprises a gaze detection module for tracking a gaze location of the clinician as the characteristic indicative of the clinician's attention and comparing the gaze location to a location of each image to detect the lapse in attention.

8. The system of claim 7, wherein the gaze detection module is configured to determine clinical abnormalities in the images by analyzing the image data set, wherein the gaze detection module is configured to track the gaze location and compare the gaze location to the location of the clinical abnormalities.

9. The system of claim 1, wherein the attention detection module, comprises a vigilance loss detection module for determining the characteristic indicative of the clinician's attention by a difference between a first baseline measure of vigilance based on a first distribution of blinks during a first time period and a second baseline measure to a second distribution of blinks during a second time period.

10. The system of claim 1, wherein the attention detection module, comprises a facial movement detection module for determining the characteristic indicative of the clinician's attention based on facial features focused along a line of sight to the image.

11. The system of claim 10, wherein the facial movement detection module is configured to use a facial recognition algorithm to determine facial features of the clinician.

12. A method, comprising:

sequentially displaying images from an image data set at a predetermined rate on a display;

monitoring a characteristic indicative of a clinician's attention to a displayed image of the image data set with an optical attention monitoring device;

detecting a lapse in attention of the clinician to at least one of the displayed images based on the characteristic indicative of the clinician's attention; and re-displaying the at least one of the displayed images in response to the detecting of the lapse in attention characterized in that detecting a lapse in attention comprises analyzing a time period of blink duration or an exposure of a pupil as the characteristic indicative of the clinician's attention and determining the lapse based on the time period of blink duration exceeding a predetermined blink threshold or based on a time period of pupil loss exceeding a predetermined pupil threshold.

13. The method of claim 12, further comprising:

superimposing a graphical attention status bar over the displayed images, wherein the graphical attention status bar includes a first bar indicating an order of the sequential display of the displayed images and one or more segments superimposed over the first bar that correspond to the at least one of displayed images presented during the lapse in attention.

14. The method of claim 13, further comprising:

re-displaying at least one of displayed images in response to an input indicative of a selection of at least one of the one or more segments by the clinician.

15. A computer readable storage medium encoded with computer readable instructions, which, when executed by a processor, causes the processor to carry out the steps of the method described in claim 12.

16. The system according to claim 1, wherein the optical attention monitoring device is an optical sensor, a camera, or a device worn by the clinician containing an optical sensor or camera.

17. The system according to claim 1, wherein the optical attention monitoring device and/or the display are integrated with a computing system containing at least a processor and an input device.

* * * * *